United States Patent
Peng et al.

(10) Patent No.: US 10,288,549 B2
(45) Date of Patent: May 14, 2019

(54) DETECTION DEVICE AND METHOD FOR IMPROVING LAYER-TO-LAYER TRANSITION OF STEEL WIRE ROPES

(71) Applicant: CHINA UNIVERSITY OF MINING AND TECHNOLOGY, Jiangsu (CN)

(72) Inventors: Yuxing Peng, Jiangsu (CN); Zhencai Zhu, Jiangsu (CN); Wenxue Xu, Jiangsu (CN); Zhiyuan Shi, Jiangsu (CN); Xiansheng Gong, Jiangsu (CN); Xiangdong Chang, Jiangsu (CN); Dagang Wang, Jiangsu (CN); Guohua Cao, Jiangsu (CN); Songyong Liu, Jiangsu (CN)

(73) Assignee: CHINA UNIVERSITY OF MINING AND TECHNOLOGY, Jiangsu (CN)

( * ) Notice: Subject to any disclaimer, the term of this patent is extended or adjusted under 35 U.S.C. 154(b) by 0 days.

(21) Appl. No.: 16/079,521

(22) PCT Filed: Mar. 2, 2017

(86) PCT No.: PCT/CN2017/075380
§ 371 (c)(1),
(2) Date: Aug. 23, 2018

(87) PCT Pub. No.: WO2017/148401
PCT Pub. Date: Sep. 8, 2017

(65) Prior Publication Data
US 2019/0094127 A1  Mar. 28, 2019

(30) Foreign Application Priority Data
Mar. 4, 2016  (CN) .......................... 2016 1 0124152

(51) Int. Cl.
*G01N 19/02* (2006.01)
*G01L 5/06* (2006.01)

(52) U.S. Cl.
CPC .............. *G01N 19/02* (2013.01); *G01L 5/06* (2013.01)

(58) Field of Classification Search
CPC ................................. G01N 19/02; G01L 5/06
(Continued)

(56) References Cited

U.S. PATENT DOCUMENTS

| | | | |
|---|---|---|---|
| 4,633,702 A * | 1/1987 | Kaiser | G01N 19/02 73/168 |
| 2003/0201431 A1* | 10/2003 | Theurer | B60M 1/28 254/134.3 R |
| 2019/0031474 A1* | 1/2019 | Stilborn | B66C 13/16 |

FOREIGN PATENT DOCUMENTS

| | | |
|---|---|---|
| CN | 1932472 A | 3/2007 |
| CN | 2854575 Y | 3/2007 |

(Continued)

OTHER PUBLICATIONS

Translation of CN-103383342 Gao (Year: 2013).*
(Continued)

*Primary Examiner* — Nathaniel T Woodward
(74) *Attorney, Agent, or Firm* — Masuvalley & Partners

(57) ABSTRACT

Systems and methods for detecting a layer-to-layer transition of a lifting steel wire rope on a reel are described. The system includes a reel assembly for winding a steel wire rope on a reel and a tensioning assembly for tensioning a segment of said steel wire rope. The system further includes a loading assembly and a lead screw sliding assembly. The loading assembly provides a vertical loading to the tensioning assembly so as to generate a loading force between the tensioned steel wire rope and the steel wire rope wound around the reel. The lead screw sliding assembly drives the tensioning assembly so as to move on a horizontal guide rail to generate a relative displacement between the tensioned steel wire rope and the steel wire rope wound around the (Continued)

reel. The tensioning assembly is connected to the loading assembly via a first threaded rod and a static torque sensor.

20 Claims, 6 Drawing Sheets

(58) Field of Classification Search
USPC .............................................................. 73/9
See application file for complete search history.

(56) References Cited

FOREIGN PATENT DOCUMENTS

| | | | | |
|---|---|---|---|---|
| CN | 101216397 A | | 7/2008 | |
| CN | 103383342 | * | 11/2013 | ............ G01N 19/02 |
| CN | 104316424 A | | 1/2015 | |
| CN | 104458566 A | | 3/2015 | |
| CN | 104634686 A | | 5/2015 | |
| CN | 104729987 A | * | 6/2015 | ............ G01N 19/00 |
| CN | 104729987 A | | 6/2015 | |
| CN | 105584944 A | | 5/2016 | |

OTHER PUBLICATIONS

ISA/CN, International Search Report dated Jun. 1, 2017 in International Patent Application No. PCT/CN2017/075380, total 6 pages.

\* cited by examiner

US 10,288,549 B2

DETECTION DEVICE AND METHOD FOR IMPROVING LAYER-TO-LAYER TRANSITION OF STEEL WIRE ROPES

RELATED APPLICATIONS

This application is the U.S. National phase of International Application No. PCT/CN2017/075380 filed on Mar. 2, 2017, and claims priority to Chinese Patent Application No. 201610124152.1, filed on Mar. 4, 2016, which are hereby expressly incorporated by reference in their entirety for all purposes.

TECHNICAL FIELD

The present invention relates to a device and a method for detecting layer-to-layer transition of a lifting steel wire rope, applicable to simulating friction and vibration behaviors and states of a steel wire rope when the steel wire rope is wound around a reel and is about to form a further layer, so as to provide a detection means suitable for the design and optimization of multi-layer winding of a lifting and winding device.

BACKGROUND OF THE DISCLOSURE

Lifting and winding devices are usually used in engineering fields, such as for example, in various hoisting machines and mine hoists. During operation, a steel wire rope may bear various loads at the same time such as tensioning, bending, twisting, and compressing, and may also experience various mechanical damages. These are related to a working condition of the steel wire rope. In many cases, single-layer winding cannot adequately meet the function requirements. On the other hand, the appropriate use of a multi-layer winding of a steel wire rope needs further research. For multi-layer winding of a steel wire rope, the wire rope will form another layer when the winding within previous layer is finished. During transitioning from the previous layer to the next layer, the steel wire rope undergoes complex forces and frictions, which greatly affect the service life of the steel wire rope. Studying the friction behavior of the steel wire rope in this stage provides an important theoretical guide for appropriately designing a multi-layer winding reel and improving the service life of the steel wire rope, and additionally, it has a practical engineering value. Therefore, there is a great need for a method and device to detect the friction force of a steel wire rope when the steel wire rope is wound around a reel and is about to form a further layer.

SUMMARY OF THE INVENTION

An objective of the present invention is to provide a friction detection device and an experimental method capable of comprehensively simulating and measuring tensile force on a steel wire rope, friction force between the steel wire ropes, and twisting force on the steel wire rope when the steel wire rope is wound around a reel for multiple layers and about to form a further layer.

Technical solutions of the present invention are as follows:

In accordance with a first aspect of the present invention, there is provided a device for detecting a layer-to-layer transition of a lifting steel wire rope. The device may include a reel assembly, a steel wire rope tensioning assembly, a steel wire rope loading assembly, and a lead screw sliding assembly, wherein the reel assembly is used to wind a steel wire rope around a reel, and can drive the reel to rotate; the steel wire rope tensioning assembly is used to tension a steel wire rope; the steel wire rope loading assembly is used to provide vertical loading for the steel wire rope tensioning assembly, so that loading force is generated between the tensioned steel wire rope and the steel wire rope wound around the reel; the lead screw sliding assembly is used to drive the steel wire rope tensioning assembly to move on a guide rail (2), so that there is a relative displacement between the tensioned steel wire rope and the steel wire rope wound around the reel; the reel assembly and the lead screw sliding assembly are mounted on a bottom frame (1); the steel wire rope tensioning assembly is connected to the steel wire rope loading assembly via a threaded rod and a static torque sensor (28); the steel wire rope loading assembly is sleeved on vertical bare shaft guide rails (4) via sliding blocks (9); and lower parts of the vertical bare shaft guide rails (4) are fixed to a rack that is slideable along a horizontal guide rail (2).

The reel assembly may include the reel (12), a torque sensor (23), and a first variable frequency motor (10), the first variable frequency motor (10) drives the reel (12) to rotate, and the torque sensor (23) is connected between the variable frequency motor (10) and the reel (12), and measures torque on the reel (12) in real time.

In this embodiment, the steel wire rope tensioning assembly may include a linear tensioning assembly and a curvilinear tensioning assembly. The linear tensioning assembly is configured to tension the steel wire rope when the steel wire rope is in a linear state, and the curvilinear tensioning assembly is configured to tension the steel wire rope when the steel wire rope is in a curved or polyline state.

In the device for detecting layer-to-layer transition of a lifting steel wire rope, the linear tensioning component includes a steel wire rope tensioning plate (29), a support device (36), a tensioning sliding block (25B), a tension and compression sensor (35), a first hook (34A), a second hook (34C), and a second threaded rod; the support device (36) is fixed to one end of the steel wire rope tensioning plate (29), a guide rail is disposed inside the support device (36), the guide rail provides guiding and support for the tensioning sliding block (25B), one side of the tensioning sliding block (25B) is fixedly connected to the second threaded rod (38), an internal thread matching the threaded rod (38) is disposed on the support device (36), and the second threaded rod (38) is rotated to drive the tensioning sliding block (25B) to slide on the guide rail of the support device 36; the other side of the tensioning sliding block (25B) is connected to the tension and compression sensor (35), the first hook (34A) is mounted on the tension and compression sensor (35), the first hook (34A) is used to hook one end of the steel wire rope, the second hook (34C) is fixed to the other end of the steel wire rope tensioning plate (29) and hooks the other end of the steel wire rope, the other end of the steel wire rope tensioning plate (29) is connected to a second middle-side plate (41B) via the static torque sensor (28), the tension and compression sensor (35) can measure, in real time, tension and compression force acting on the steel wire rope, and the static torque sensor (28) measures, in real time, static torque acting on the steel wire rope.

The curvilinear tensioning assembly includes bare shaft sliding rails (37), fixable sliding blocks (40), a first side plate (39), a second side plate (39B), a third hook (34B), a fourth hook (34D), a guide device (26), a first tensioning sliding block (25), and a first threaded rod (27); there are four bare shaft sliding rails (37), which are provided as two groups each with two bare shaft sliding rails and respectively fixed to a first middle-side plate (41) and a second middle-side plate (41B) of a middle plate (30), the first side plate (39) and the second side plate (39B) are respectively sleeved on the bare shaft sliding rails (37) via two fixable sliding blocks (40), and the first side plate (39) and the second side plate (39B) may slide up and down along the bare shaft sliding rails (37) as a whole, and are fixed via the fixable sliding blocks (40); the guide device (26) is fixed to the second side plate (39B), a rail is disposed inside the guide device (26), and a groove on the first tensioning sliding block (25) matches with the rail, so that the first tensioning sliding block (25) can slide along the guide device (26); the first threaded rod (27) matches with a threaded hole on the second side plate (39B), one end of the first threaded rod (27) is fixedly connected to the first tensioning sliding block (25), the first threaded rod (27) is rotated to drive the first tensioning sliding block (25) to move along the rail, to tension the steel wire rope hooked on the third hook (34B) and the fourth hook (34D), and by sliding the first side plate (39) and the second side plate (39B) up and down along the bare shaft sliding rails (37), a curvature of the steel wire rope pressed on the reel can be adjusted, and friction performance related to layer-to-layer transition of the steel wire rope in a curved state can be detected.

In one embodiment, fixable sliding blocks (40) may be locked at any location on bare shaft sliding rails (37), and when the locked locations of the fixable sliding blocks (40) are adjusted, a location of an end of the steel wire rope hooked on a side plate (39) changes, so that a curvature of the steel wire rope can be adjusted.

The lead screw sliding assembly according to the embodiments of the present invention may include a second variable frequency motor (15), a lead screw (17), and a horizontal guide rail (2); the second variable frequency motor (15) drives, via a coupling, the lead screw (17) to rotate, so that a lead screw sliding block (18) on the lead screw (17) makes a horizontal displacement, one end of the lead screw sliding block (18) is connected to a first tension and compression sensor (19), the first tension and compression sensor (19) is fixed to a beam (20), a sliding rail on which the steel wire rope tensioning assembly is located and a sliding rail on which the steel wire rope loading assembly is located are fixed together, and when the second variable frequency motor (15) is started, the lead screw sliding block (18) on the lead screw (17) makes a horizontal displacement, so that the steel wire rope tensioning assembly and the steel wire rope loading assembly can slide along the horizontal guide rail (2) as a whole; and the first tension and compression sensor (19) is used to measure friction force between a straight steel wire rope and the steel wire rope wound around the reel or between a curved steel wire rope and the steel wire rope wound around the reel at different angles when the lifting steel wire rope being wound on the reel transitions layer-to-layer.

In another embodiment, the device for detecting the layer-to-layer transition of the lifting steel wire rope further includes a clump weight which is attached to a press plate (31) via a threaded rod (33), and a different clump weight may be fixed as required; four external corners of the press plate (31) are fitted on the vertical bare shaft guide rails (4) via bare shaft sliding blocks (9), so that the entire device can slide up and down along the vertical guide rails; arc-shaped slots are formed on the press plate (31), and fit with threaded rods on a middle plate (30), so that the middle plate (30) is fixed to the press plate (31); the middle plate (30) can rotate relative to the press plate (31) via the arc-shaped slots, to implement friction between the steel wire ropes at different angles one side of the steel wire rope tensioning assembly is connected to a support device via the static torque sensor (28), the other side of the steel wire rope tensioning assembly is connected to the middle plate (30) via a tensioning threaded rod (38), the entire steel wire rope tensioning assembly can rotate around the center of the tensioned steel wire rope (32), and the static torque sensor (28) can measure torque experienced by the steel wire rope (32); the tensioning assembly is provided with a tensioning sliding block, and the tensioning sliding block may be dragged via the threaded rod (38) to tension the steel wire rope; a tension and compression sensor (35) is disposed between the tensioning sliding block and the steel wire rope (32), and can measure and control a magnitude of tensile force on the steel wire rope (32); the tension and compression sensor (35) and the steel wire rope (32) are connected by using a hook (34A), so that rope changing is convenient; bare shaft sliding rails (37) and fixable sliding blocks (40) are disposed on two sides of the middle plate (30), so that two side plates (39) and the middle plate (30) are connected; and the two side plates (39) may be locked at different locations of the bare shaft sliding rails (37) via the fixable sliding blocks (40), to implement arc-shaped friction between the steel wire ropes.

According to the first embodiment, the steel wire rope loading assembly is used to exert a pressure in a vertical direction to a to-be-measured steel wire rope, and includes a press plate (31) and a middle plate (30); four identical sliding blocks (9) are mounted on an external side of the press plate (31), the sliding blocks (9) are sleeved on four identical vertical bare shaft guide rails (4), so that the press plate (31) can slide up and down freely within a range along the vertical bare shaft guide rails (4); a middle part of the press plate (31) is connected to the middle plate (30) via a bolt, two symmetric arc-shaped slots (21) are formed on the press plate (31), and the press plate (31) and the middle plate (30) are connected by using the two arc-shaped slots (21); and the middle plate (30) can rotate horizontally relative to the press plate (31) by a particular angle, to implement different-angle friction between the steel wire rope hooked on the hooks and the steel wire rope on the reel.

In accordance with a second aspect of the present invention, there is provided a method for detecting a layer-to-layer transition of a steel wire rope on a multi-layer winding reel, the method comprising the steps of: the method comprising the steps of:

attaching a steel wire rope wound on a reel to a steel wire rope tensioning plate via a first and a second hook, or via a third and a fourth hook;

rotating a first threaded rod or a second threaded rod to tension the steel wire rope retained between the hooks;

placing a clump weight on a press plate for compressing the steel wire rope retained between the hooks against the steel wire rope wound on the reel, wherein a compression force between the steel wire ropes can be controlled by adjusting the clump weight, said clump weight being attached to the press plate using a threaded rod and a bolt;

driving a lead screw to rotate, using a variable frequency motor, thereby moving horizontally a lead screw sliding block along said lead screw, so as to drive a steel wire rope tensioning assembly and a steel wire rope loading assembly to move horizontally along a horizontal guide rail as a whole, allowing friction to occur between the steel wire rope on the hooks and the steel wire rope wound on the reel due to said relative sliding; and determining a friction performance of a layer-to-layer transition of the steel wire ropes by:

rotating a middle plate horizontally along arc-shaped slots on the press plate so as to change an angle between said middle plate and said press plate, implementing a different-angle friction between the steel wire ropes, and/or moving fixable sliding blocks on bare shaft sliding rails so as to adjust vertically a position of side plates on said bare shaft sliding rails, rubbing the steel wire ropes in a curved state, and by driving the reel to rotate using another variable frequency to create a more complex friction, wherein a torque sensor measures an output torque of another variable frequency motor, a first tension and compression sensor measures a frictional resistance between the steel wire ropes, a second tension and compression sensor measures a tensile force on the steel wire rope, and a static torque sensor measures a torque experienced by the steel wire rope.

Beneficial effects: in the present invention, a frictional behavior of a steel wire rope when the steel wire rope is wound around a reel for multiple layers and about to form a further layer can be simulated and measured. The main advantages may include:

1. A friction and vibration behaviors between layers of steel wire ropes when the steel wire rope is wound around the reel for multiple layers and about to form a further layer can be simulated, and tensile force on a straight steel wire rope and tensile force on a curved steel wire rope, twisting force on the straight steel wire rope, and friction force and vibration acceleration between a wound steel wire rope, the straight steel wire rope, and the curved steel wire rope can be measured in real time during layer-to-layer transition.
2. The contact angle, contact load, contact rotational speed, and displacement speed between a wound steel wire rope, a straight steel wire rope, and a curved steel wire rope can be adjusted, thereby implementing different-angles, different-loads, and different-speed friction detections.
3. Rope changing is easy and efficiency is relatively high.
4. The structure is simple, and functions are reliable.

BRIEF DESCRIPTION OF DRAWINGS

The present disclosure is described in conjunction with the appended figures.

Figure 1:
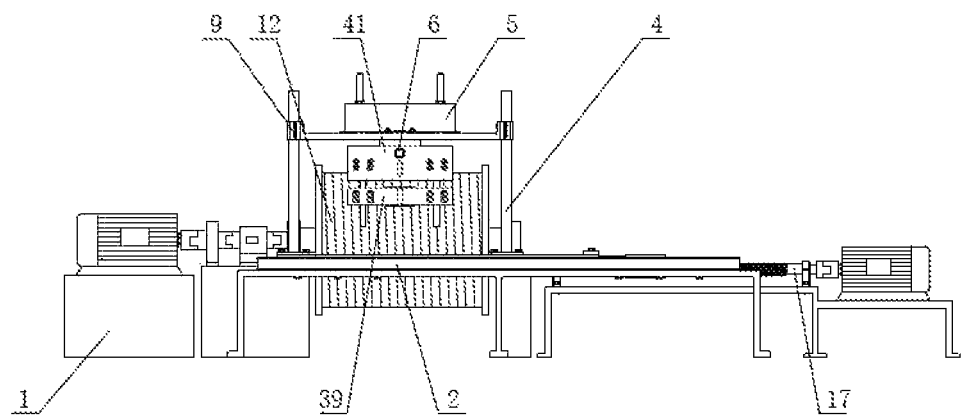
FIG. 1 depicts schematically a side view of an embodiment a device for detecting a layer-to layer transition of a lifting steel wire rope according to the present invention.

In the appended figures, similar components and/or features may have the same reference numeral, wherein like reference numerals refer to like parts throughout the various views unless otherwise specified. For ease of understanding, the main components are listed below with their corresponding reference numerals: 1: support base, 2: horizontal guide rail, 4: vertical bare shaft guide rail, 5: clump weight, 6: vibration acceleration sensor, 9: sliding block, 10: first variable-frequency motor, 11: coupling, 12: reel, 13: reel shaft, 14: coupling, 15: second variable-frequency motor, 16: lead screw base, 17: lead screw, 18: lead screw sliding block, 19: first tension and compression sensor, 20: beam, 21: arc-shaped slot, 22: bearing seat, 23: torque sensor, 24: coupling, 25: first tensioning sliding block, 25B: second tensioning sliding block, 26: guide device, 27: first threaded rod, 28: static torque sensor, 29: steel wire rope tensioning plate, 30: middle plate, 31: press plate, 32: steel wire rope, 33: threaded rod, 34A: first hook, 34B: second hook, 34C: third hook, 34D fourth hook, 35: second tension and compression sensor, 35B: third tension and compression sensor, 36: support device, 37: bare shaft sliding rail, 38: second threaded rod, 39: first side plate, 39B: second side plate, 40: fixable sliding block, 41: first middle-side plate, 41B: second middle-side plate, 42: middle plate rotation guide shaft, 43: middle plate fixation shaft.

DETAILED DESCRIPTION OF THE INVENTION

The following describes in detail the present invention with reference to specific embodiments.

As shown in FIG. 1, a device for detecting layer-to-layer transition of a lifting steel wire rope includes a reel assembly, a steel wire rope tensioning assembly, a steel wire rope loading assembly, and a lead screw sliding assembly, where the reel assembly is used to wind a steel wire rope around a reel, and can drive the reel to rotate; the steel wire rope tensioning assembly is used to tension a steel wire rope; the steel wire rope loading assembly is used to provide vertical loading for the steel wire rope tensioning assembly, so that loading force is generated between the tensioned steel wire rope and the steel wire rope wound around the reel; the lead screw sliding assembly is used to drive the steel wire rope tensioning assembly to move on a guide rail 2, so that there is a relative displacement between the tensioned steel wire rope and the steel wire rope wound around the reel; the reel assembly and the lead screw sliding assembly are mounted on a support base 1; the steel wire rope tensioning assembly is connected to the steel wire rope loading assembly via a threaded rod and a static torque sensor 28; the steel wire rope loading assembly is sleeved on vertical bare shaft guide rails 4 via sliding blocks 9; and lower parts of the vertical bare shaft guide rails 4 are fixed to a rack that is slideable along a horizontal guide rail 2.

Figure 3:
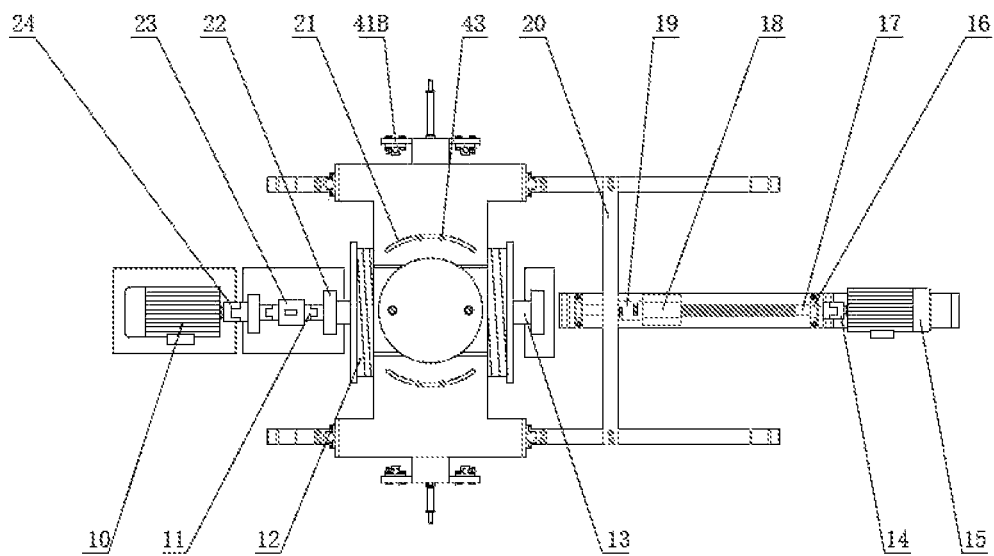
FIG. 3 depicts schematically a top view of the device of FIG. 1.
Figure 4:
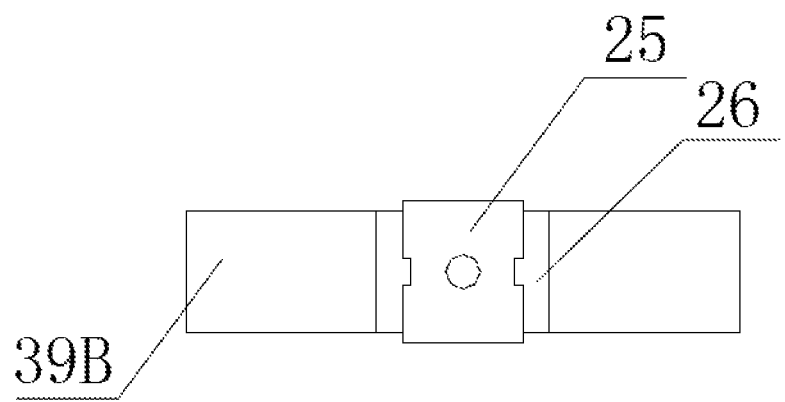
FIG. 4 depicts schematically a top view of an embodiment of a first tensioning sliding block, a guide device, and a side plate of a curvilinear tensioning assembly.
Figure 5:
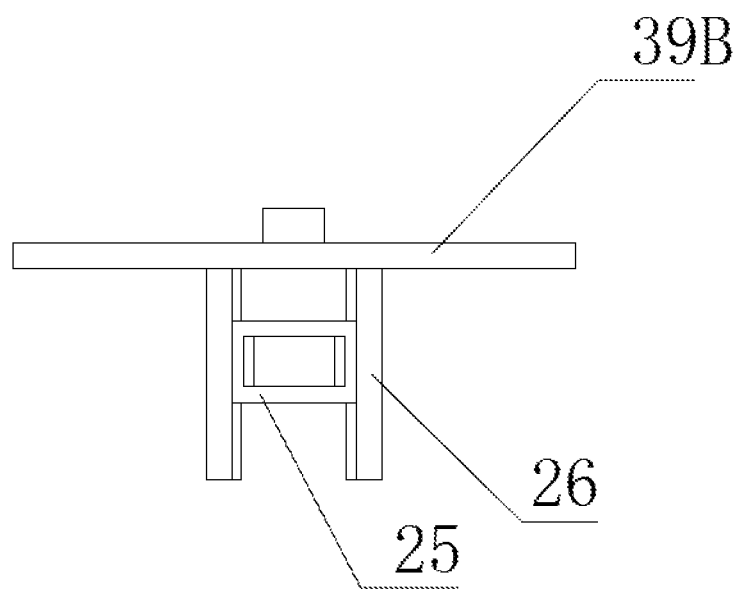
FIG. 5 depicts schematically a side view of an embodiment of a first tensioning sliding block, a guide device, and a side plate of a curvilinear tensioning assembly.
Figure 6:
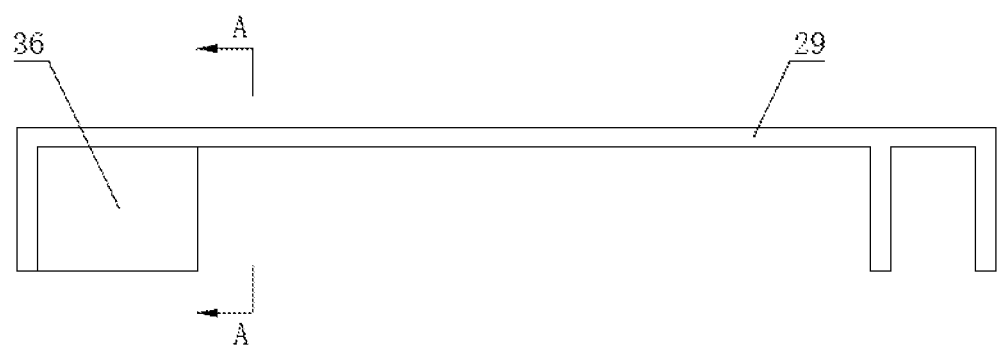
FIG. 6 depicts a schematic side view of a steel wire rope tensioning plate and a support device in a steel wire rope tensioning assembly.
Figure 7:
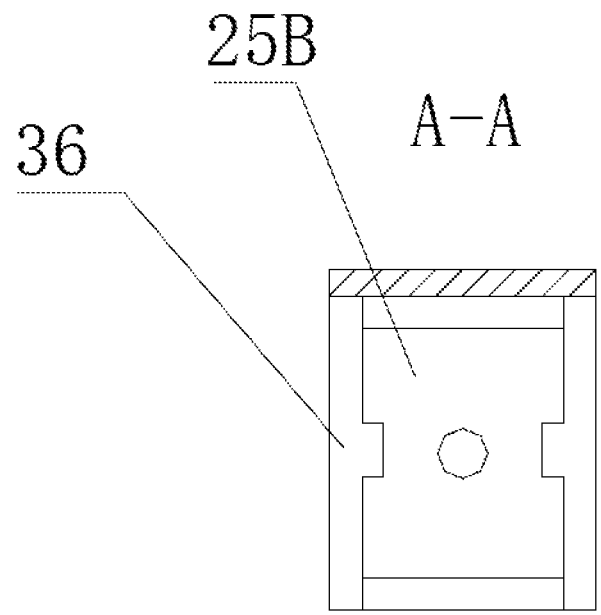
FIG. 7 is a sectional view depicting an embodiment of the support device and the second sliding block along the line A-A of FIG. 6.
Figure 8:
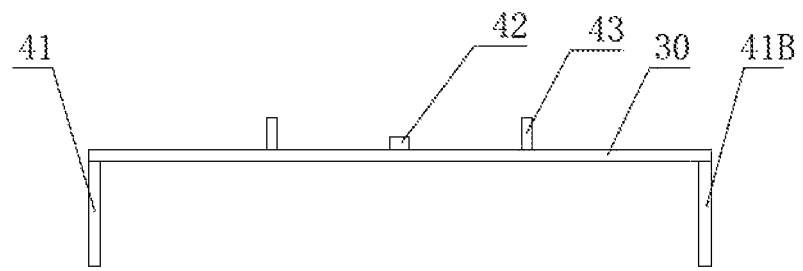
FIG. 8 depicts a schematic side view of an embodiment a middle plate of FIG. 2.
Figure 9:
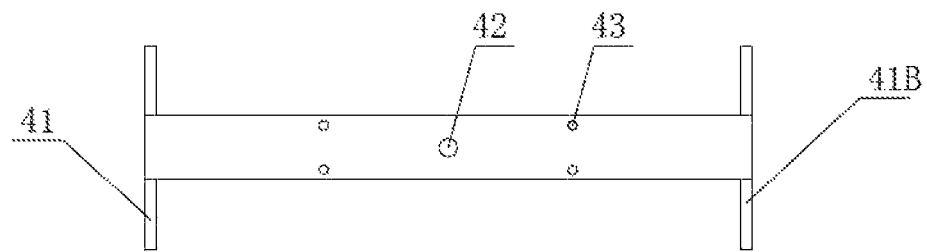
FIG. 9 depicts a schematic top view of the middle plate of FIG. 8.

Referring to FIG. 3, the reel assembly includes the reel 12, a torque sensor 23, and a first variable frequency motor 10, the first variable frequency motor 10 drives the reel 12 to rotate, and the torque sensor 23 is connected between the variable frequency motor 10 and the reel 12, and measures torque on the reel 12 in real time.

Referring to FIG. 2 and FIG. 4 to FIG. 11, the steel wire rope tensioning assembly includes a linear tensioning assembly and a curved tensioning assembly. The linear tensioning assembly can tension the steel wire rope when the steel wire rope is in a linear state, and the curvilinear tensioning assembly can tension the steel wire rope in a curved state. The linear tensioning assembly includes a steel wire rope tensioning plate 29, a support device 36, a tensioning sliding block 25B, a tension and compression sensor 35, a first hook 34A, a second hook 34C, and a second threaded rod 38. The support device 36 is fixed to one end of the steel wire rope tensioning plate 29, a guide rail is disposed inside the support device 36, and the guide rail provides guiding and support for the tensioning sliding block 25B. One side of the tensioning sliding block 25B is fixedly connected to the second threaded rod 38, an internal thread matching the threaded rod 38 is disposed on the support device 36, and when the second threaded rod 38 is rotated to drive the tensioning sliding block 25B to slide on the guide rail of the support device 36. The other side of the tensioning sliding block 25B is connected to the tension and compression sensor 35. The first hook 34A is disposed on the tension and compression sensor 35, and the first hook 34A is used to retain one end of the steel wire rope 32. The second hook 34C is fixed to the other end (right end) of the steel wire rope tensioning plate 29, and retains the other end of the steel wire rope 32. The other end of the steel wire rope tensioning plate 29 is connected to the second middle-side plate 41B via the static torque sensor 28. The tension and compression sensor 35 can measure, in real time, tension and compression force acting on the steel wire rope. The static torque sensor 28 measures, in real time, static torque acting on the steel wire rope.

The curvilinear tensioning assembly includes bare shaft sliding rails 37, fixable sliding blocks 40, a first side plate 39, a second side plate 39B, a third hook 34B, a fourth hook 34D, a guide device 26, a first tensioning sliding block 25, and a first threaded rod 27; there are four bare shaft sliding rails 37, which are provided as two groups each with two bare shaft sliding rails and respectively fixed to a first middle-side plate 41 and a second middle-side plate 41B of a middle plate 30, the first side plate 39 and the second side plate 39B are respectively sleeved on the bare shaft sliding rails 37 via two fixable sliding blocks 40, and the first side plate 39 and the second side plate 39B may slide up and down along the bare shaft sliding rails 37 as a whole, and are fixed via the fixable sliding blocks 40; the guide device 26 is fixed to the second side plate 39B, a rail is disposed inside the guide device 26, and a groove on the first tensioning sliding block 25 matches with the rail, so that the first tensioning sliding block 25 can slide along the guide device 26; the first threaded rod 27 matches with a threaded hole on the second side plate 39B, one end of the first threaded rod 27 is fixedly connected to the first tensioning sliding block 25, the first threaded rod 27 is rotated to drive the first tensioning sliding block 25 to move along the rail, to tension the steel wire rope hooked on the third hook 34B and the fourth hook 34D, and the first side plate 39 and the second side plate 39B slide up and down on the bare shaft sliding rails 37, so that a curvature of the steel wire rope pressed on the reel can be adjusted, and friction performance related to layer-to-layer transition of the steel wire rope in a curved state can be detected.

The steel wire rope loading assembly is used to exert a pressure in a vertical direction to a to-be-measured steel wire rope, and includes a press plate 31 and a middle plate 30; four identical sliding blocks 9 are mounted on an external side of the press plate 31, the sliding blocks 9 are sleeved on four identical vertical bare shaft guide rails 4, so that the press plate 31 can slide up and down freely within a range along the vertical bare shaft guide rail 4; a middle part of the press plate 31 is connected to the middle plate 30 via a bolt, two symmetric arc-shaped slots 21 are formed on the press plate 31, and the press plate 31 and the middle plate 30 are connected by using the two arc-shaped slots 21; and the middle plate 30 can rotate horizontally relative to the press plate 31 by a particular angle, to implement different-angle friction between the steel wire rope hooked on the hooks and the steel wire rope on the reel.

Figure 10:
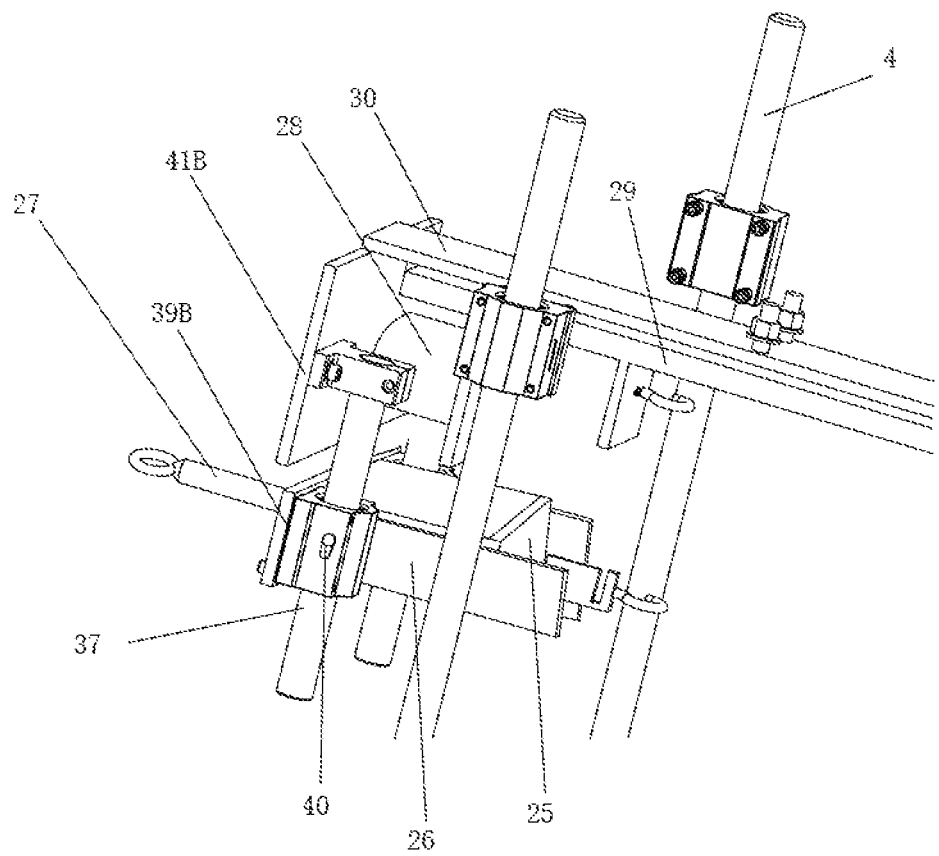
FIG. 10 illustrates an enlarged right hand side portion of FIG. 2, depicting in greater clarity various components of the steel wire rope tensioning assembly.
Figure 11:
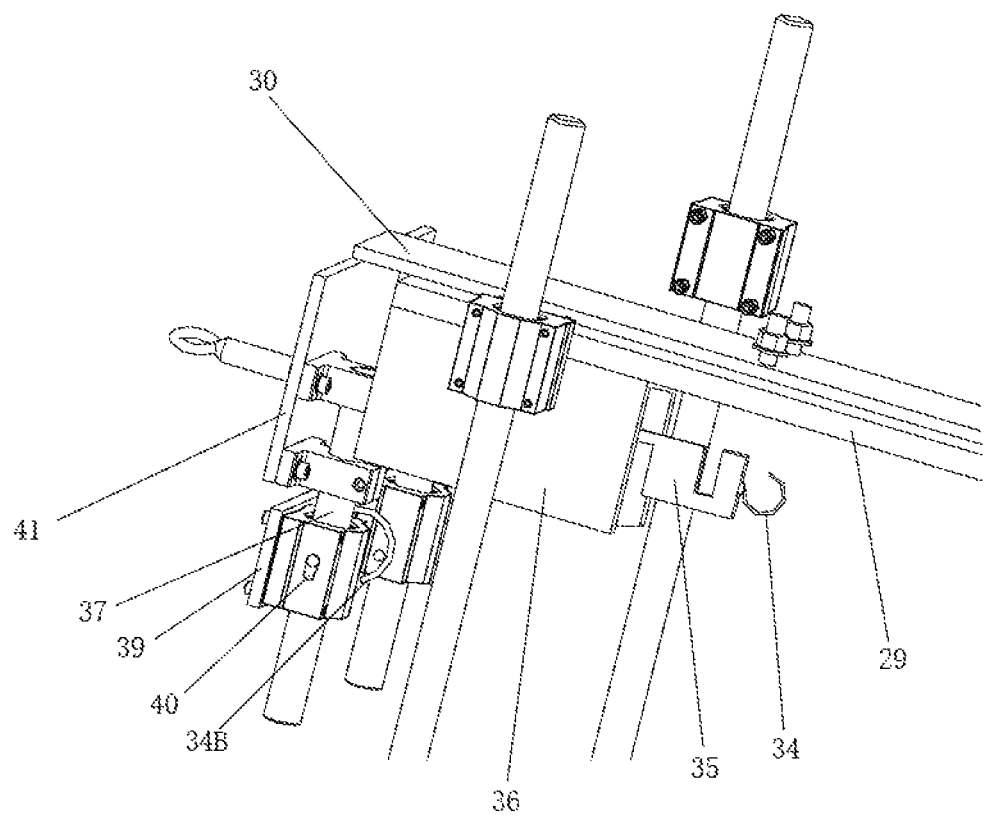
FIG. 11 illustrates an enlarged left hand side portion of FIG. 2, depicting in greater clarity various components of the steel wire rope tensioning assembly.

Referring to FIG. 10 and FIG. 11, two side plates at two ends of the middle plate 30 are respectively connected to two groups of horizontal bare shaft seats via bolts. Each group of horizontal bare shaft seat is used to fix two identical bare shaft sliding rails 37. The fixable sliding blocks 40 are sleeved on the bare shaft sliding rails 37. The fixable sliding blocks 40 are fixed to the side plates 39. The third hook 34B is mounted on one side plate 39, and is used to hook the steel wire rope. The third hook 34B and the fourth hook 34D are used cooperatively, so that the steel wire rope straddles on the reel 12 in a curved (or referred to as a polyline) shape.

Referring to FIG. 10 and FIG. 1, the fixable sliding blocks 40 may be locked at any location on the bare shaft sliding rails 37, and when the locked locations of the fixable sliding blocks 40 are adjusted, a location of an end of the steel wire rope (for clarity and unambiguity, the steel wire rope is not shown) hooked on the side plate 39 changes, so that a curvature of the steel wire rope can be adjusted.

The lead screw sliding assembly includes a second variable frequency motor 15, a lead screw 17, and a horizontal guide rail 2; the second variable frequency motor 15 drives, via a coupling, the lead screw 17 to rotate, so that a lead screw sliding block 18 on the lead screw 17 makes a horizontal displacement, one end of the lead screw sliding block 18 is connected to a first tension and compression sensor 19, the first tension and compression sensor 19 is fixed to a beam 20, a sliding rail on which the steel wire rope tensioning assembly is located and a sliding rail on which the steel wire rope loading assembly is located are fixed together, and when the second variable frequency motor 15 is started, the lead screw sliding block 18 on the lead screw 17 makes a horizontal displacement, so that the steel wire rope tensioning assembly and the steel wire rope loading assembly can slide along the horizontal guide rail 2 as a whole; and the first tension and compression sensor 19 is used to measure friction force between a straight steel wire rope and the steel wire rope wound around the reel or between a curved steel wire rope and the steel wire rope wound around the reel at different angles when the lifting steel wire rope being wound on the reel transitions layer-to-layer.

Figure 2:
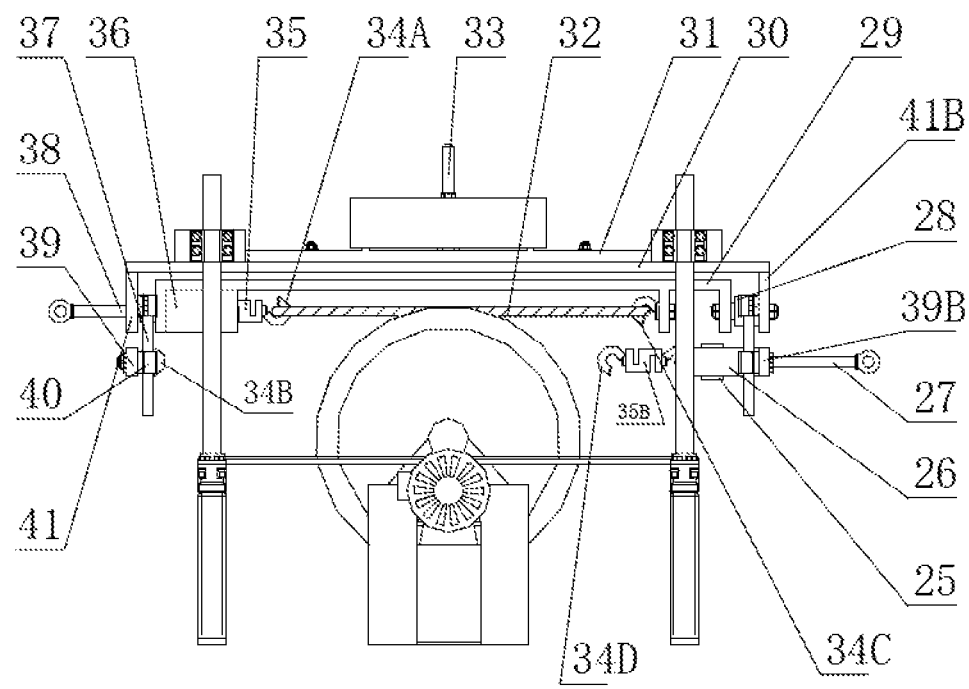
FIG. 2 depicts schematically a front view of the device of FIG. 1.

As shown in FIG. 2, a clump weight 5 is fixed to a press plate 31 via a threaded rod 33, and a different clump weight may be fixed as required; four external corners of the press plate 31 are fitted on the vertical bare shaft guide rails 4 via bare shaft sliding blocks 9, so that the entire device can slide up and down along the vertical guide rails 4; arc-shaped slots are formed on the press plate 31, and fit with threaded rods on a middle plate 30, so that the middle plate 30 is fixed to the press plate 31; the middle plate 30 can rotate relative to the press plate 31 via the arc-shaped slots, to implement friction between the steel wire ropes at different angles one side of the steel wire rope tensioning assembly is connected to a support device 36 via the static torque sensor 28, the other side of the steel wire rope tensioning assembly is connected to the middle plate 30 via a tensioning threaded rod 38, the entire steel wire rope tensioning assembly can rotate around the center of the tensioned steel wire rope 32, and the static torque sensor 28 can measure torque experienced by the steel wire rope 32; the tensioning assembly is provided with a tensioning sliding block, and the tensioning sliding block may be dragged via the threaded rod 38 to tension the steel wire rope; a tension and compression sensor 35 is disposed between the tensioning sliding block and the steel wire rope 32, and can measure and control a magnitude of tensile force on the steel wire rope 32; the tension and compression sensor 35 and the steel wire rope 32 are connected by using a hook 34A, so that rope changing is convenient; bare shaft sliding rails 37 and fixable sliding blocks 40 are disposed on two sides of the middle plate 30, so that two side plates 39 and the middle plate 30 are connected; and the two side plates 39 may be locked at different locations of the bare shaft sliding rails 37 via the fixable sliding blocks 40, to implement arc-shaped friction between the steel wire ropes.

A method for detecting layer-to-layer transition of a lifting steel wire rope in the present invention includes the following steps:

1. winding and fixing a steel wire rope to a reel 12;
2. fixing a steel wire rope to a steel wire rope tensioning plate 29 via a first hook 34A and a second hook 34B, or via a third hook 34C and a fourth hook 34D, and rotating a second threaded rod 38 or a first threaded rod 27, to tension the steel wire rope;
3. placing a clump weight 5 on a press plate 31, compressing the steel wire rope on the hooks against the steel wire rope on the reel tightly, and controlling compression force between the steel wire ropes by adjusting the clump weight, and fixing the clump weight 5 to the press plate 31 using the threaded rod 33 and a bolt; and
4. controlling a second variable frequency motor 15 to drive a lead screw 17 to rotate, so that a lead screw sliding block 18 moves horizontally along the lead screw 17, to drive a steel wire rope tensioning assembly and a steel wire rope loading assembly to move horizontally along a horizontal guide rail 2 as a whole, and friction occurs between the steel wire rope on the hooks and the steel wire rope on the reel due to relative sliding.

In a case where, different-angles of a layer-to-layer transition friction performance of the steel wire ropes need to be detected, the method further includes a step of rotating a middle plate 30 horizontally, so that the middle plate 30 rotates along arc-shaped slots 21 on the press plate 31, and an included angle between the middle plate 30 and the press plate 31 can be changed, to implement different-angle friction between the steel wire ropes. On the other hand, if a layer-to-layer transition friction performance of the steel wire ropes in a curved state needs to be detected, the method further includes a step of moving fixable sliding blocks 40 on the bare shaft sliding rails 37, so that side plates 39 can be adjusted to move up and down, and the steel wire rope rubs in an curved shape, and controlling a first variable frequency motor 10 to drive the reel 12 to rotate, so that a more complex friction situation can be measured, where a torque sensor 23 is used to measure output torque of the first variable frequency motor 10, a first tension and compression sensor 19 is used to measure frictional resistance between the steel wire ropes, a second tension and compression sensor 35 is used to measure tensile force on the steel wire rope, and a static torque sensor 28 is used to measure torque experienced by the steel wire rope.

It should be understood that a person of ordinary skill in the art may make improvements or changes according to the foregoing descriptions, and these improvements and changes shall fall within the scope of the appended claims of the present invention.

What is claimed is:

1. A device for detecting a layer-to-layer transition of a lifting steel wire rope, the device comprising:
   a reel assembly configured to wind a steel wire rope around a reel and to drive said reel to rotate;
   a steel wire rope tensioning assembly configured to provide a tension on a segment of the steel wire rope;
   a steel wire rope loading assembly configured to provide a vertical loading to the steel wire rope tensioning assembly so as to generate a loading force between the segment of steel wire rope and the steel wire rope wound around the reel; and
   a lead screw sliding assembly configured to drive the steel wire rope tensioning assembly to move on a horizontal guide rail to generate a relative displacement between the the segment of steel wire rope and the steel wire rope wound around the reel,
   wherein the steel wire rope tensioning assembly is connected to the steel wire rope loading assembly via a first threaded rod and a static torque sensor.

2. The device according to claim 1, wherein the reel assembly and the lead screw sliding assembly are mounted on a support base.

3. The device according to claim 1, wherein the steel wire rope loading assembly is sleeved on vertical bare shaft guide rails via sliding blocks, and wherein lower parts of said vertical bare shaft guide rails are fixed to a rack which is slidable along the horizontal guide rail.

4. The device according to claim 1, wherein the reel assembly comprises a reel, a torque sensor, and a first variable frequency motor.

5. The device according to claim 4, wherein the first variable frequency motor is configured to drive the reel to rotate, and the torque sensor, which is connected between the first variable frequency motor and the reel, is configured to measure a torque applied on said reel in real time.

6. The device according to claim 4, wherein the lead screw sliding assembly comprises a second variable frequency motor, a lead screw, and a horizontal guide rail, wherein:
   the second variable frequency motor is configured to rotate the lead screw, via a coupling, so that a lead screw sliding block disposed on said lead screw makes a horizontal displacement, one end of said lead screw sliding block being connected to a first tension and compression sensor which is fixedly attached to a beam,
   when the second variable frequency motor starts operating the steel wire rope tensioning assembly and the steel wire rope loading assembly start sliding along the horizontal guide rail as a whole, each of said steel wire rope tensioning assembly and steel wire rope loading assembly being disposed on a separate sliding rail which are attached together, and
   the first tension and compression sensor is configured to measure a friction force between the segment of steel wire rope and the steel wire rope wound around the reel at different angles when the steel wire rope being wound on the reel making its transition to the next layer.

7. The device according to claim 1, wherein the steel wire rope tensioning assembly further comprises a linear tensioning assembly and a curvilinear tensioning assembly, wherein the linear tensioning assembly is configured to tension the segment of steel wire rope in a linear state, while the curvilinear tensioning assembly is configured to tension the segment of steel wire rope in a curved or polyline state.

8. The device according to claim 7, wherein the linear tensioning assembly comprising:
   a steel wire rope tensioning plate;
   a tensioning sliding block;
   a support device being fixedly attached to one end of the steel wire rope tensioning plate where a guide rail being disposed inside said support device to provide guiding and support for the tensioning sliding block;
   a first hook and a second hook for retaining detachably both ends of the segment of steel wire rope, said first hook being connected to a tension and compression sensor while the second hook being fixedly connected to the other end of the steel wire rope tensioning plate, wherein:
   one side of the tensioning sliding block is fixedly connected to a second threaded rod, while the other side of the tensioning sliding block is connected to the tension and compression sensor,
   said tension and compression sensor is able to measure, in real time, tension and compression forces acting on the segment of steel wire rope.

9. The device according to claim 8, wherein an internal thread matching the second threaded rod is disposed in the support device, wherein a rotation of said second threaded rod drives the tensioning sliding block to slide on the guide rail of said support device.

10. The device according to claim 8, wherein the other end of the steel wire rope tensioning plate is connected to a middle-side plate of a middle plate via a static torque sensor, said static torque sensor is capable of measuring in real time a static torque acting on said steel wire rope.

11. The device according to claim 7, wherein the curvilinear tensioning assembly comprising:
   a first set of rails having two bare shaft sliding rails attached to a first middle-side plate at one end of a middle plate, wherein a first side plate is sleeved on the bare shaft sliding rails in the first set of rails, said first side plate sliding up and down along each of said bare shaft sliding rails and is able to be locked in a position via a first fixable sliding block;
   a second set of rails having two bare shaft sliding rails attached to a second middle-side plate at the other end of the middle plate, wherein a second side plate is sleeved on the bare shaft sliding rails in the second set of rails, said second side plate sliding up and down along said bare shaft sliding rails and is able to be locked in a position via a second fixable sliding block;
   a first tensioning sliding block configured to slide along a guide device, said guide device being fixedly attached to the second side plate and being disposed internally to a rail matching a groove on said first tensioning sliding block;
   a first threaded rod matching a threaded hole on the second side plate where one end of said first threaded rod being fixedly attached to the first tensioning sliding block, said first threaded rod is configured to rotate so as to drive said first tensioning sliding block moving along the rail, thereby tensioning the segment of steel wire rope retained between a third hook and a forth hook.

12. The device according to claim 11, wherein a curvature of the segment of steel wire rope pressed on the reel is adjustable by sliding the first side plates and the second side plates along the bare shaft sliding rails in the first and second sets of rails, thereby a friction performance of the layer-to layer transition of the lifting steel wire rope can be detected.

13. The device according to claim 11, wherein the first and second fixable sliding blocks are able to be locked at any location on each of the bare shaft sliding rails in the first and second sets of rails, and wherein a curvature of the segment of steel wire rope retained on its respective side plate can be adjusted, once a locked position of said first and second fixable sliding blocks is adjusted.

14. The device according to claim 7 further comprising a clump weight detachably attached to a press plate via a threaded rod, wherein four external corners of said press plate are fitted on vertical bare shaft guide rails via sliding blocks, allowing the entire device to slide up and down along the vertical bare shaft guide rails, wherein arc-shaped slots are formed on said press plate fitting threaded rods disposed on a middle plate so as to attach said middle plate to said press plate, and wherein the middle plate is able to rotate relative to the press plate via the arc-shaped slots, thereby implementing a friction between the segment of steel wire rope and the steel wire rope wound around the reel at different angles.

15. The device according to claim 14, wherein one side of the steel wire rope tensioning assembly is connected to a guide device via the static torque sensor, while the other side of the steel wire rope tensioning assembly is connected to the middle plate via a tensioning threaded rod, so that an entire steel wire rope tensioning assembly is rotatable around a center of the tensioned steel wire rope, and the static torque sensor is capable of measuring a torque experienced by said tensioned steel wire rope.

16. The device according to claim 15, wherein the steel wire rope tensioning assembly is further comprising:
   a tensioning sliding block configured to be pulled via the tensioning threaded rod so as to tension the segment of steel wire rope;
   a tension and compression sensor, disposed between said tensioning sliding block and said segment of steel wire rope, to measure and control a magnitude of a tensile force applied on segment of said steel wire rope, wherein the segment of steel wire rope is connected to said tension and compression sensor using a hook; and
   bare shaft sliding rails and fixable sliding blocks are disposed on two sides of the middle plate, so as to connect said middle plate to two side plates which are capable being locked at different locations on said bare shaft sliding rails via the fixable sliding blocks, thereby implementing arc-shaped friction between the segment of steel wire rope and the steel wire rope wound around the reel.

17. The device according to claim 1, wherein the steel wire rope loading assembly is configured to exert a pressure on the segment of steel wire rope in a vertical direction and is comprising a press plate and a middle plate.

18. The device according to claim 17, wherein four sliding blocks are mounted on an external side of the press plate while being sleeved on four vertical bare shaft guide rails so that the press plate is able to freely slide up and down within a range along said four vertical bare shaft guide rails.

19. The device according to claim 18, wherein a middle part of the press plate is connected to the middle plate via a bolt, and two symmetric arc-shaped slots are formed on the press plate connecting said press plate to the middle plate such that said middle plate is able to rotate horizontally relative to the press plate by a particular angle, thereby implementing different-angle friction between the segment of steel wire rope retained on separate hooks and the steel wire rope wound around the reel.

20. A method for detecting a layer-to-layer transition of a steel wire rope on a multi-layer winding reel, the method comprising the steps of:

attaching a segment of a steel wire rope wound on a reel to a steel wire rope tensioning plate via a first and a second hook, or via a third and a fourth hook;

rotating a first threaded rod or a second threaded rod to tension the segment of steel wire rope retained between the hooks;

placing a clump weight on a press plate for compressing the segment of steel wire rope retained between the hooks against the steel wire rope wound on the reel, wherein a compression force between the segment of steel wire rope retained between the hooks against the steel wire rope wound on the reel can be controlled by adjusting the clump weight, said clump weight being attached to the press plate using a threaded rod and a bolt;

driving a lead screw to rotate, using a variable frequency motor, thereby moving horizontally a lead screw sliding block along said lead screw, so as to drive a steel wire rope tensioning assembly and a steel wire rope loading assembly to move horizontally along a horizontal guide rail as a whole, allowing friction to occur between the segment of steel wire rope retained between the hooks and the steel wire rope wound on the reel due to said relative sliding; and determining a friction performance of a layer-to-layer transition of the steel wire ropes by:

rotating a middle plate horizontally along arc-shaped slots on the press plate so as to change an angle between said middle plate and said press plate, implementing a different-angle friction between the segment of steel wire rope retained between the hooks and the steel wire rope wound on the reel, and/or moving fixable sliding blocks on bare shaft sliding rails so as to adjust vertically a position of side plates on said bare shaft sliding rails, rubbing the segment of steel wire rope retained between the hooks in a curved state against the steel wire rope wound on the reel, and by driving the reel to rotate using another variable frequency motor to create a complex friction, wherein a torque sensor measures an output torque of another variable frequency motor, a first tension and compression sensor measures a frictional resistance between the segment of steel wire rope retained between the hooks and the steel wire rope wound on the reel, a second tension and compression sensor measures a tensile force on the segment of steel wire rope retained between the hooks, and a static torque sensor measures a torque experienced by the segment of steel wire rope retained between the hooks.

\* \* \* \* \*